(12) United States Patent
Chakrabarti

(10) Patent No.: US 8,415,315 B2
(45) Date of Patent: Apr. 9, 2013

(54) METHODS AND COMPOSITIONS FOR INHIBITING THE PROLIFERATION OF CANCER CELLS

(75) Inventor: Ratna Chakrabarti, Winter Springs, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 86 days.

(21) Appl. No.: 12/706,218

(22) Filed: Feb. 16, 2010

(65) Prior Publication Data

US 2011/0251255 A1 Oct. 13, 2011

Related U.S. Application Data

(63) Continuation of application No. 10/840,737, filed on May 6, 2004, now abandoned.

(51) Int. Cl.
*C12N 15/11* (2006.01)
*A61K 48/00* (2006.01)
*C07H 21/02* (2006.01)
*C07H 21/04* (2006.01)

(52) U.S. Cl.
USPC ........................................ 514/44 A; 536/24.5

(58) Field of Classification Search .................... 514/44; 536/24.5
See application file for complete search history.

(56) References Cited

U.S. PATENT DOCUMENTS

| | | | |
|---|---|---|---|
| 4,806,561 A | 2/1989 | Anderson | |
| 4,985,445 A | 1/1991 | Tsuruoka et al. | |
| 5,250,545 A | 10/1993 | Tsuruoka et al. | |
| 5,716,846 A | 2/1998 | Brown et al. | |
| 5,750,515 A | 5/1998 | Shibata et al. | |
| 5,863,898 A | 1/1999 | Goli et al. | |
| 5,955,443 A | 9/1999 | Bennett et al. | |
| 5,958,731 A | 9/1999 | Yue et al. | |
| 6,174,702 B1 | 1/2001 | Lal et al. | |
| 6,184,211 B1 | 2/2001 | Szyf | |
| 6,255,314 B1 | 7/2001 | Miyadera et al. | |
| 6,265,547 B1 | 7/2001 | Yue et al. | |

(Continued)

FOREIGN PATENT DOCUMENTS

WO  WO 01/30964 A2 * 10/2000
WO  WO 02099048 A2    12/2002

OTHER PUBLICATIONS

Davila et al. (Journal of Biological Chemistry, 2003 vol. 278:36868-36875).*
Yoshioka et al. (PNAS, 2003 vol. 100:7247-7252).*

(Continued)

*Primary Examiner* — Terra Cotta Gibbs
(74) *Attorney, Agent, or Firm* — Timothy H. Van Dyke; Beusse, Wolter, Sanks, Mora & Maire, P.A.

(57) ABSTRACT

A method of decreasing the expression of LIM kinase 1 in a cancer cell comprising; providing an oligonucleotide consisting of the sequence of SEQ ID NO: 1; providing a cancer cell comprising an mRNA encoding LIM kinase 1; and introducing the oligonucleotide into the cancer cell, wherein the oligonucleotide decreases the expression of LIM kinase 1 in the cancer cell. The method also provides compositions of an antisense RNA LIM kinase 1 that can be administered to an individual for the purpose of inhibiting a protein kinase pathway and which further comprises methods for treating and monitoring the proliferation and metastasis of cancer cells. A kit may be used in the detection and treatment of cancer.

7 Claims, 6 Drawing Sheets

U.S. PATENT DOCUMENTS

| | | | |
|---|---|---|---|
| 6,309,849 B1 | 10/2001 | Robison | |
| 6,340,583 B1 | 1/2002 | Yan et al. | |
| 6,358,711 B1 | 3/2002 | Lal et al. | |
| 6,455,283 B1 | 9/2002 | Ferrara et al. | |
| 6,544,784 B1 | 4/2003 | Bullerdiek et al. | |
| 6,558,903 B1 | 5/2003 | Hodge | |
| 6,566,351 B1 | 5/2003 | Ogata et al. | |
| 6,576,608 B1 | 6/2003 | Lee et al. | |
| 6,579,856 B2 | 6/2003 | Mercola | |
| 6,602,851 B1 | 8/2003 | Carroll | |
| 6,630,335 B1 | 10/2003 | Kapeller-Libermann | |
| 6,656,969 B2 | 12/2003 | Young | |
| 6,664,288 B1 | 12/2003 | Pardee et al. | |
| 6,683,082 B2 | 1/2004 | Tang et al. | |
| 2004/0014047 A1 | 1/2004 | Cowsert et al. | |
| 2004/0142946 A1 | 7/2004 | Chattopadhyaya | |

OTHER PUBLICATIONS

"Identification of a human cDNA encoding a novel protein kinase with tow repeats of the LIM/double zinc finger motif," Mizuno, K., Okano, I., Ohashi, K., Nunoue, K., Kuma, K., Miyata, T., Nakamura, T. (1994) *Oncogene* 6, 1605-1612.

"c-erbB-2/neu Overexpression Enhances Metastatic Potential of Human Lung Cancer Cells by Induction of Metastasis-associated Properties," Yu, D., Wang, S., Dulski, K.M., Tsai, C, M., Nicolson, G.L., and Hung, M.C. (1994) *Cancer Res.* 54, 3260-3266.

"Kiz-1, a Protein with LIM Zinc Finger and Kinase Domains, is Expressed Mainly in Neurons," Bernard, D., Geniatsus, S., Kannourakis, G., and Dringen, R. (1994) *Cell Growth Differ.* 5, 1159-1171.

"Rho, Rac, and Cdc42Pases Regulate the Assembly of Multimolecular Focal Complexes Associated with Actin Stress Fibers, Lamellipodia, and Filopodia," Nobes, C.D., and Hall, A. (1995) *Cell* 81, 53-62.

"Identification and Characterization of a Novel Family of Serine-Threonine Kinases Containing Two N-terminal LIM Motifs," Okano, I., Hiraoka, J., Otera, H., Nunoue, K., Ohashi, K., Iwashita, S., Hirai, M., and Mizuno, K. (1995) *J. Biol. Chem.* 270, 31321-31330.

"Suppression of fibroblast cell browth by overexpression of LILM-Kinase 1," Higuchi, O., Baeg, G., Akiyama, T., and Mizuno, K. (1996) *FEBS Lett.* 396, 81-86.

"Inhibition of activated Ras-induced neuronal differentiation of PC12 cells by the LIM domain of LIM-kinase 1," Higuchi, O., Amano, T., Yang, N. and Mizuno, K. 91997)*Oncogene* 14, 1819-1825.

"Interphase Cytogenetics of Prostatic Tumor Progression: Specific Chromosomal Abnormalities are Involved in Metastasis to the Bone," Alers, J. C., Krijtenburg, P. J., Rosenberg, C., Hop, W. C. J., Verkerk, A.M., Schroder, F. H., van der Kwast, Th. H., Bosman, F. T., and Dekken, H. (1997) *Lab. Invest.* 77, 437-48.

"Transmembrane Neuregulins Interact with LILM Kinase 1, a Cytoplasmic Protein Kinase Implicated in Development of Visuospatial Cognition," Wang, J. Y., Frenzel, K.E., Wen, D., and Falls, D. (1998) *J. Biol. Chem.* 273, 20525-20534.

"Regulation of actin dynamics through phosphorylation of cofilin by LIM-kinase," Arber, S., Barbayannis, F. A., Hanser, H., Schneider, C., Stanyon, C. A., Bernard, O., and Caroni, P. (1998)*Nature* 393, 805-809.

"Rho GTPasses and the Actin Cytoskeleton," Hall, A. (1998) *Science* 279, 509-514.

"Cofilin phosphorylation by LIM-kinase 1 and its role in Rac-mediated actin reorganization,"Yang, N., Higuchi, O., Ohashi, K., Nagata, K., Wada, A., Kangawa, K., Nishida, E., and Mizuno, K. (1998) *Nature* 393, 809-812.

"Cytoplasmic Localization of LIT-Kinase 1 is Directed by a Short Sequence within the PDZ Domain," Yang, N., Higuchi, O., and Mizuno, K. (1998) *Exp. Cell Res.* 241, 242-252.

"Cell Cycle-independent Death of Prostate Adenocarcinoma Is Induced by the trk Tyrosine Kinase Inhibitor CEP-751 (KT6587)," Dionne, C, A., Camoratto, A. M., Jani, J. P. Emerson, E., Neff, N., Vaught, J. L., Murakata, C., Djakiew, D., Lamb, J., Bova, S., George, D., and Issacs, J.T. (1998) *Clin. Cancer Res.* 4, 1887-1898.

"The Transcrition Factor AP-1 id Required for EGF-induced activation of Rho-like GTPases, Cytoskeletal Rearrangements, Motility, and in Vitro Invasion of A431 Cells," Malliri, A., Symons, M., Hennigan, R. F., Hurlstone, A. F., Wheeler, T., and Ozanne, B. W. (1998) *J. Cell Biol.* 143, 1087-1099.

"ARF1 Mediates Paxillin Recruitment to Focal Adhesions and Potentiates Pho-stimulated Stress Fiber Formation in Intact and Permeabilized Swiss 3T3 Fibroblasts," Norman, J.C., Jones, D., Barry, S. T., Holt, M. R., Cockcroft, S., and Critchley, E. R. (1998) *J. Cell Biol.* 143, 1981-1995.

"Longitudinal Evaluation of Cytogenetic Aberrations in Prostatic Cancer: Tumours that Recur in Time Display and Intermediate Genetic Status Between Non-Persistent and Metastatic Tumours," Alers, J. C., Krijtenburg, P. J., Hop, W. C., Bolle, W. A., Schroder, F. H., van der Kwast, T. H., Bosman, F. T., and van Dekken, H. (1998) *J. Pathol.* vol. 185, 273-283.

"Role of neurotrophins and neurotrophin receptors in the 'in vitro' invasion and heparanase production of human prostate cancer cells," Walch, E. T., and Marchetti, D. (1999) *Clin Esp. Metastasis* 17, 307-314.

"Activation of LIM-kinase by Pak1 couples Rac/Cdc42 GTPase signaling to actin cytoskeletal dynamics," Edwards, D., and Gill, G. N. (1999) *J. Biol. Chem*, 274, 11352-11361.

"Proteins of the ADF/Cofilin Family: Essential Regulators of Actin Dynamics," Bamburg, J.R., (1999) *Annu. Rev. Cell Dev. Biol.* 15, 185-230.

"Cofilin Phosphorylation and Actin Cytoskeletal Dynamics Regulated by Rho-and Cdc42-activated LIM-kinase 2," Sumi, T., Matsumoto, K., Takai, Y., and Nakamura, T. (1999) *J. Cell Biol.* 147, 1519-1532.

"Structural Features of LIM Kinase That Control Effects on the Actin Cytoskeleton," Edwards, D. C., Sanders, L. C., Bokoch, G. M. and Gill, G. N., (1999) *Nat. Cell Biol.* 1, 253-259.

"Functional design in the actin cytoskeleton," Small, J.V., Rottner, K., and Kaverina, I. (1999) *Curr. Opin. Cell boil.* 11, 54-60.

"Prognostic Value of Immunohistochemical Expression of the c-erbB-2 Oncoprotein in Metastasic Prostate Cancer," Morote, J., Torres, I., Caceres, C., Vallejo, C., Schwartz, S., and Reventos, J. (1999) *Int.J. Cancer* 84, 421-425.

"Actin Cytoskeleton Organization in Response to Integrin-Mediated Adhesion," Defilippi, P., Olivo, C., Venturino, M., Dolce, L., Silengo, L., and Tarone, G. (1999) *Microsc. Res. Tech.* 47, 67-78.

"Membrane Type 1-Matrix Metalloproteinase (MTI-MMP) and MMP-2 Immunolocalization in Human Prostate: Change in Cellular Localization Associated with High-Grade Prostatic Intraepithelial Neoplasia," Upadhyay, J., Shekarriz, B., Nemeth, J. A., Dong, Z., Cummings, G.D., Fridman, R., Sakr, W., Grignon, D. J., and Cher, M.L. (1999) *Clin. Cancer Res.* 5, 4105-4110.

"Membrane-type matrix metalloproteinases." Seiki, M.(1999) *APMIS* 107, 137-143.

"Identification of Genetic Markers for Prostatic Cancer Progression," Alers, J. C., Rochat, J., Krijtenburg, P. J., Hop, W. C., Kranse, R., Rosengerg, C., Tanke, H. J., Schroder, F. H., and van Dekken, H. (2000) *Lab. Invest* 80, 931-942.

"Paxillin and focal adhesion signaling," Turner, C. E., (2000) *Nat. Cell Biol*, 2, 231-236.

"Rho-Kinase Inhibitor Retards Migration and 'in Vivo' Dissemination of Human Prostate Cancer Cells," Somlyo, A. V., Bradshaw, D., Ramos, S., Murphy, C., Myers, C. E., and Somlyo,, A. P., (2000) *Biochem. Biophys. Res. Commun.* 269, 652-659.

"Rho-associated Kinase ROCK Activates LIM-Kinase 1 by Phosphorylation at Threonine 508 within the Activation Loop," Ohashi, K., Nagata, K., Maekawa, M., Ishizaki, T., Narumiya, S., and Mizuno, K. (2000) *J. Biol. Chem.* 275, 3577-3582.

"Expression of membrane-type 1 matrix metalloproteinase (MT1-MMP) on prostate cancer cell lines," Nagakawa, O., Murakami, K., Yamaura, T., Fujiuchi, Y., Murata, J., Fuse, H., and Saiki, I., (2000) *Cancer Lett.* 155, 173-179.

"Regulation of Cell Invasion and Morphogenesis in a Three-dimensional Type 1 Collagen Matrix by Membrane-type Matrix Metalloproteinase 1, 2, and 3," Hotary, K., Allen, E., Punturieri, A., Yana, I., and Weiss, S. J. (2000) *J. Cell Biol.* 149, 1309-1323.

"A Protein Kinase from Neutrophils That Specifically Recognizes Ser-3 in Cofilin," Lian, J. P., Marks, P. G., Wang, J. Y., Falls, D. L., and Badwey, J. A., (2000) *J. Biol. Chem.* 275, 2869-2876.

"Molecular Cytogenetic Analysis of Prostatic Adenocarcinomas from Screening Studies," Alers, J.C., Krijtenburg, P. J., Vis, A.N., Hoedemaeker, R. F., Wildhagen, M.F., Hop, W. C., van Der Kwast, T. T., Schroder, F. H., Tanke, H. J., and van Dekken, H. (2001) *Am. J. Pathol.* 158, 399-406.

"Homophilic complex formation of MTI-MMP facilitates proMMP-2 activation on the cell surface and promotes tumor cell invasion," Itoh, Y., Takamura, A., Ito, N., Maur, Y., Sato, H., Suenaga, N., Aoki, T. and Seiki, M. (2001) *EMBO J.* 20, 4782-4793.

"Deletions at Chromosome Regions 7q11.23 and 7q36 in a Patient with Williams Syndrome," Wouters, C.H., Meijers-Heijboer, H. J., Eussen, B. J., van der Heide, A.A., van Luijk, R. B., van Drunen, E., Beverloo, B. B., Visscher, F., and Van Hemel, J.O. (2001) *Am. J. Med. Genet.* 102, 261-265.

"Cytoskeletal Changes Regulated by the PAK4 Serine/Threonine Kinase Are Mediated by LIM Kinase ! and Cofilin," Dan, C., Kelly, A., Bernard, O., and Minden, A. (2001) *J. Biol. Chem.* 276, 32115-32121.

"Activation of LIM Kinases by Myotonic Dystrophy Kinase-related Cdc42-binding Kinase a," Sumi, T., Matsumoto, K., Shibuya. A., and Nakamura, T. (2001) *J. Biol. Chem.* 276, 23092-23096.

"Delineation of prognostic biomarkets in prostate cancer," Dhanasekaran, S. M., Barrette, T. R. Ghosh, D., Shah, R., Varambally, S., Kurachi, K., Pienta, K.J., Rubin, M.A., and Chinnaiyan, A. M. (2001) *Nature* 412, 822-826.

"The use of multicolor fluorescence technologies in the characterization of prostate carcinoma cell lines: a comparison of multiplex fluorescence in situ hybridization and spectral karyotyping data," Strefford, J. C., Lillington, D.M., Young, B.D., and Oliver, R. T.,(2001) *Cancer Genet. Cytogenet.* 124, 112-121.

Cofilin Phosphorylation and Actin Reorganization Activities of Testicular Protein Kinase 2 and its Predominant Expression in Testicular Sertoli Cells, Toshima, J., Toshima, J.Y., Takeuchi, K., Mori, R., and Mizuno, K. (2001) *J. Biol. Chem.* 276, 31449-31458.

"Mitosis-specific Activation of LIM Motif-containing Protein Kinase and Roles of Cofilin Phosphorylation and Dephosphorylation in Mitosis," Amano, T., Kaji, N., Ohashi, K., and Mizuno, K. (2002) *J. Biol. Chem.* 277, 22093-22102.

"Profiling of differential expression of Messenger RNA in normal, benign, and metastatic prostate cell lines," Chakrabarti, R., Robles, L. D., Gibson, J., and Muroski, M., (2002) *Cancer Genet. Cytogenet.* 139, 115-125.

"Down-regulation of Cdc6, a Cell Cycle Regulatory Gene, in Prostate Cancer," Robles, L. D., Frost, A. R., Davila, M., Hutson, A. D., Grizzle, W. E., and Chakrabarti, R. (2002) *J. Biol. Chem.* 277, 25431-25438.

"Mitosis-Dependent Phosphorylation and Activation of LIM-Kinase I," Sumi, T., Matsumoto, K., and Nakamura, T. (2002) *Biochem. Biophys. Res. Commun.* 290, 1315, 1320.

"Potential Involvement of Extracellular Signal-regulated Kinase 1 and 2 in Encystation of a Primitive Eukaryote, 'Giardia lamblia'," Ellis, J. G. Davila, M., Chakrabarti, R. (2003) *J. Biol. Chem.* 278, 1936-1945.

Pushpangadan et al. (2003) "*Antisense oligonuclotides with oxetane-constrained cytidine enhance heteroduplex stability, and elicit satisfactory RNase H response as well as showing improved resistance to both exo and endonucleases*" Org Biomol Chem. Jan. 7;1 (1):81-92.

Davila et al. (Dec. 2000) Molecular Biology of the Cell vol. 11, No. Supplement, pp. 240a. print, meeting Info.: 40th American Society for Cell Biology Annual meeting. San Francisco, CA, USA. Dec. 9-13, 2000. American Society for Cell Biology, as evidenced by Mizuno et al. (1994) Oncogene 9:1605-1612.

Higuchi et al. (1996) FEBS Lett. 396:81-86.

Mizuno et al. (1994) Oncogene 9:1605-1612.

Davila et al. (2003) J. Biol. Chem. 278:36868-37875.

Sumi et al. (2002) Biochem. Biophys. Res. Comm. 290:1315-1320.

Finn (2001) J. Natl. Cancer Institute 93:88-89.

* cited by examiner

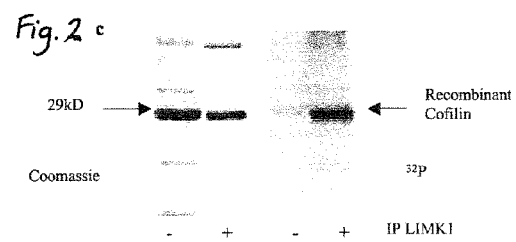
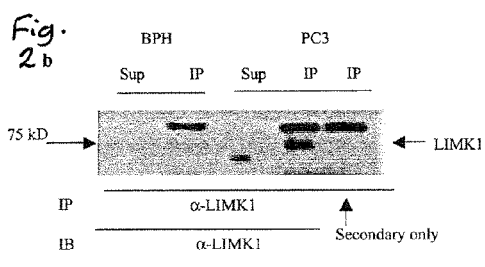
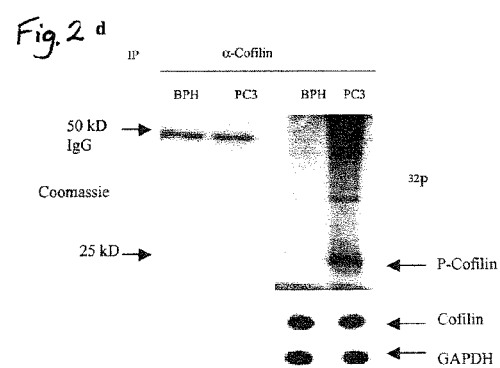
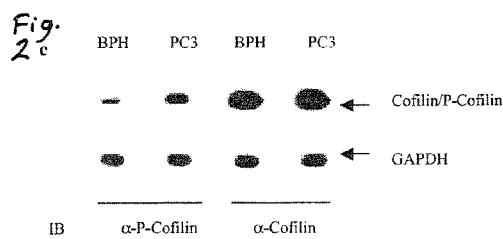

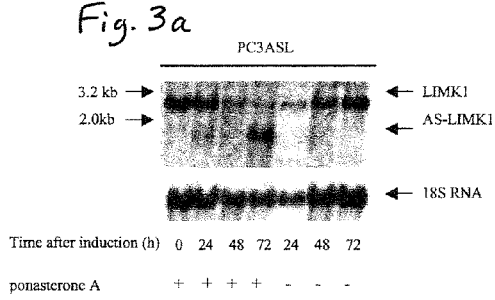
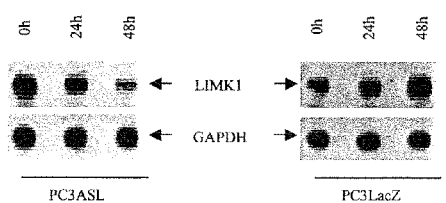
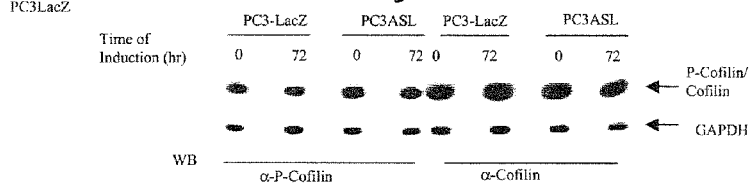

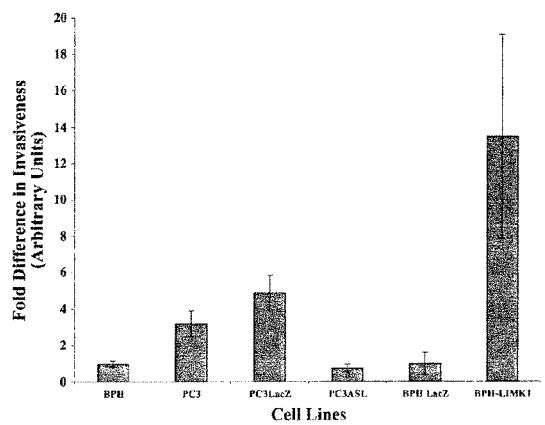
Fig. 5a
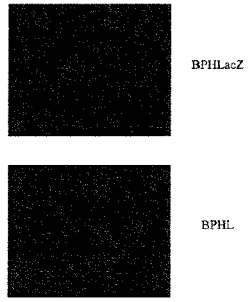
Fig. 5d
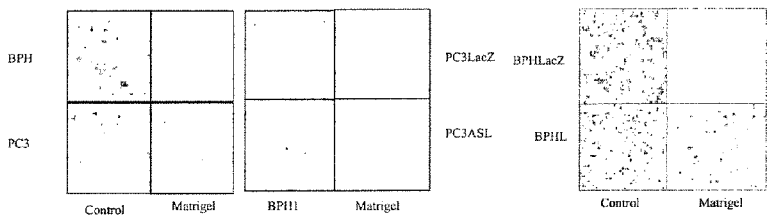
Fig. 5b
Fig. 5c

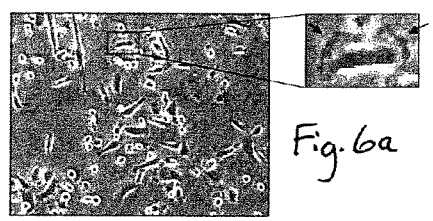
Fig. 6a
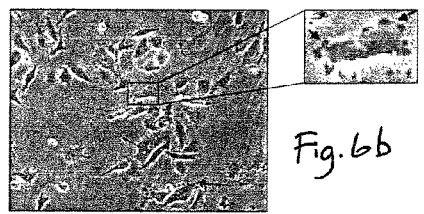
Fig. 6b
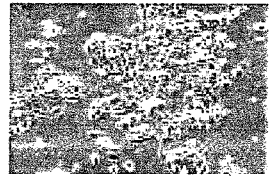
Fig. 6i
Fig. 6j
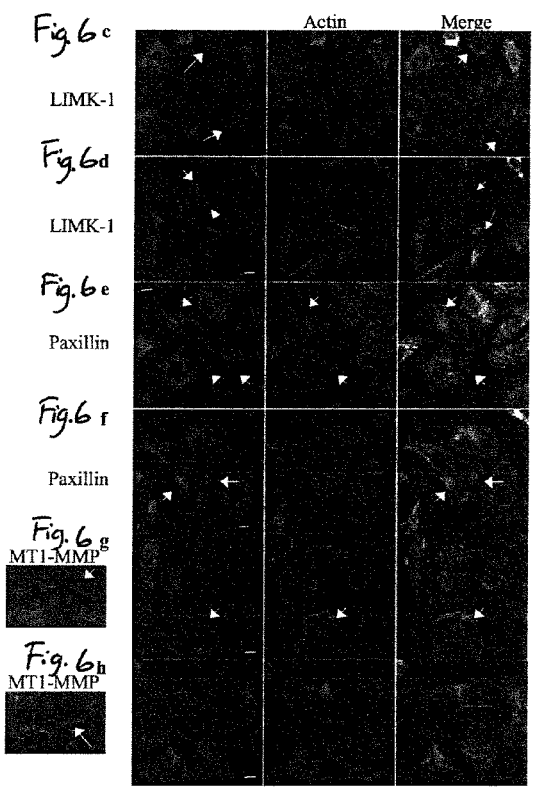
Fig. 6c LIMK-1
Fig. 6d LIMK-1
Fig. 6e Paxillin
Fig. 6f Paxillin
Fig. 6g MT1-MMP
Fig. 6h MT1-MMP

METHODS AND COMPOSITIONS FOR INHIBITING THE PROLIFERATION OF CANCER CELLS

RELATED APPLICATIONS

This application is a continuation of U.S. Ser. No. 10/840,737 filed May 6, 2004, now abandoned, which is incorporated herein in its entirety.

BACKGROUND

The following is offered as background information only and is not admitted to be prior art to the present invention.

Cancer cells are characterized by an ability to proliferate indefinitely and to invade normal tissue cells surrounding a cancerous tumor. In addition, many types of cancer cells can metastasize throughout the body whereby the tumor may be disseminated in the cancer patient's body.

The mechanism of cancer metastasis is presumed as follows: (1) cancer cells proliferate in a primary cancer colony; (2) blood vessels are newly formed; (3) the malignant cancer cells infiltrate and penetrate the newly formed blood vessels; (4) the cancer cells circulate within the human body; (5) the cancer cells reach a target organ; (6) the cancer cells extravasate from blood vessels; (7) the cancer cells proliferate in the target organ; and (8) a metastatic focus is formed.

The cure rate of malignant cancer tumors has increased with early diagnosis and with the progress of therapies, but metastases of malignant tumors are often beyond current therapies. Chemotherapies are used to arrest metastases following removal of tumors but often with unsatisfactory results. It is therefore desirable to develop more effective inhibitors against malignant tumor metastases.

Conventional methods for treating cancer have also increased the survival and quality of life for cancer patients. Such conventional methods include surgery, for example, removal of the prostate gland (radical prostectomy), radiotherapy, and chemotherapy. In addition, bone marrow transplantation is becoming useful in treating patients with certain types of cancers.

Combination therapies may be used in treating cancer and are typically not addictive. In some cases, cross effects and treatment load can result in a lower effectiveness for the combinations, than either treatment alone.

Other treatments such as radiation, while useful for a wide range of cancers, does not typically result in a complete cure. Given the severity of many cancers and the mortality rate, a drug may be thought of as successful if it improves the quality of life by delaying the growth of tumors, or if it prolongs life without actually curing the condition. In many circumstances, an individual is treated with a specific composition or with a combination of therapies that can eliminate from about 90 to about 95% of the malignant cells, but the remaining cells can re-grow and metastasize, ultimately resulting in death.

LIM kinase 1 (LIMK 1) is one of the regulatory proteins that modulate the actin cytoskeleton by inactivating an actin-binding protein, cofilin, through addition of a phosphate group to cofilin. Actin cytoskeleton is maintained by the constant severing and joining of small units of actin and any deviation away from this normal dynamic may lead to abnormal behavior of a particular cell. LIMK1 plays an important role in maintaining cell architecture through actin cytoskeleton. As an important regulator of cell behavior, levels of LIMK1 need to be regulated in cells for the maintenance of normal cellular function. The concentration of LIMK1 has previously been found at increased levels in some cancer cells; for example, cancer cells that are highly aggressive and capable of causing metastasis or the spread of tumors in mice. Research has shown that a partial inhibition of LIMK 1 synthesis using antisense RNA in these cells resulted in the inhibition of cell growth and more specifically, regression of the invasive property of these cells.

Efforts to identify compositions which inhibit the expression of LIMK 1 and, which therefore, should be useful in the treatment and prevention of cancer cell metastasis, has led to the use of the "antisense" or non-encoding LIM Kinase 1, which exhibits an ability to inhibit the expression of LIMK 1 in certain cancer cells.

Antisense RNA mediated gene therapy is a widely used method of gene inactivation and is suitable for gene therapy use. However, RNA mediated gene inactivation does not work for all genes, and may not be used as a global method of gene inactivation.

SUMMARY

Before explaining the disclosed embodiment of the present invention in detail it is to be understood that the invention is not limited in its application to the details of the particular arrangement shown since the invention is capable of other embodiments. Also, the terminology used herein is for the purpose of description and not of limitation.

In one embodiment, the present invention provides, for example, a method for treating cancers and individuals at risk of developing cancers by administering an antisense RNA of LIM Kinase 1.

In another embodiment, the present invention indicates that the expression of LIM kinase, one of the proteins that modulates actin dynamics, is over expressed in denocarcinomatous prostatic epithelium and cancer cell lines.

In one embodiment of the present invention, there is provided an advantageous therapy for inhibiting the metastasis of cancers cells, including, for example, breast, ovarian, lung, and prostate cancer cells. More specifically, the invention, in embodiments relates to the use of LIM kinase 1 antisense RNA to reduce the synthesis of endogenous LIM kinase 1 in prostate cancer cell lines. This reduction has been shown to reduce the number of metastizing cancer cells.

In another embodiment of the invention, a partial reduction of LIMK1 altered cell proliferation by arresting cells at the G2/M phase of the cell cycle. Data has also shown a changed cell shape and the associated inhibition of the invasive tendencies of metastatic prostate cancer cells. Ectopic expression of LIMK1 promotes the acquisition of the invasive phenotype by benign prostate epithelial cells. Experimental data provides evidence of a novel role of LIMK1 in regulating cell division and in regulating the invasive properties of prostate cancer cells.

In yet another embodiment of the invention, results indicate that the invasive properties of prostate cancer cells is not mediated by phosphorylation of cofilin. Experimental data correlates with the recent observations showing a metastasis-associated chromosomal gain of 7q11.2 in prostate cancer, suggesting a possible gain in LIMK1 DNA (7q11.23).

Yet another embodiment of the instant invention comprises partial amino acid and nucleotide sequences of LIMK1.

In still another embodiment of the present invention results indicate that the antisense RNA of LIM kinase 1 can be used successfully in the functional inactivation of LIM kinase 1.

In other embodiments of the present invention, antisense RNA may be used, for example, to inhibit gene function and to demonstrate that the LIMK1 gene may find use, for example, as a therapeutic target for developing effective cancer drugs.

In yet another embodiment results indicated, for the first time, that LIMK 1 may find use as a novel target for anti sense RNA mediated gene inactivation. Results also indicate that the expression of LIMK 1 may be used as a predictive marker for prostate cancer cell metastasis.

BRIEF DESCRIPTION OF THE DRAWINGS

In a further effort to make the above-recited features and aspects of the specific embodiments of the invention, clear, more specific descriptions of the invention briefly summarized above may be had by reference to embodiments thereof which are illustrated in the drawings. These drawings form a part of the specification. It is to be noted, however, that the drawings illustrate embodiments of the invention and therefore are not to be considered limiting in their scope.

FIGS. 1b and 1e show hematoxylin/eosin-stained slides at 100×.magnification.

FIGS. 1d and 1g show normal and cancerous tissues at 200× magnification. Arrows in FIGS. 1c and 1d indicate light staining in basal cells in normal/benign areas. Arrows in FIGS. 1f and 1g indicate intense staining in cells in cancerous areas. Cell lines used were PrEC and prostate epithelial cells in glyceraldehyde-3-phosphate dehydrogenase, GAPDH.

FIGS. 2a and 2b show the LIMK1 concentration in BPH-1 and PC3 cells before, FIG. 2a and after FIG. 2b immunoprecipitation with anti-LIMK1 antibody. IB immunoblot. Sup, supernatant.

FIG. 2c represents the in vitro phosphorylation of recombinant cofilin by LIMK1 immunoprecipitated from PC3 cells.

FIG. 2d shows in vivo phosphorylation of cofilin in BPH-1 and PC3 cells, and is an Immunoblot analysis of cell lysates before immunoprecipitation and shows the initial concentration of cofilin in both samples in the bottom panel of FIG. 2d.

FIG. 2e shows the immunoblot analysis of phosphorylated cofilin or cofilin in crude cell extracts using anti-phospho-cofilin or anti-cofilin antibodies.

FIGS. 3a and 3b show the RNA blot analysis of LIMK1 in PC3ASL (a) and PC3LacZ (b) cells induced successively (+) or not (−).

FIG. 3c shows the concentration of LIMK1 in transfected PC3 cells harvested at different time points after successive induction.

FIG. 3d shows the concentration of phosphorylated cofilin (P-cofilin) or cofilin in transfected PC3 cells after continuous induction. Despite the reduced concentration of LIMK1 no noticeable difference in phospho-cofilin concentration was detected in PC3ASL cells Using a Western blot in glyceraldehyde-3-phosphate dehydrogenase GAPDH. LIMK1 was effectively reduced in PC3ASL cells by expression of anti-sense LIMK1, but there was no concurrent reduction in cofilin phosphorylation.

FIG. 4b indicates the percentage of cells at different stages of the cell cycle.

FIGS. 4c and 4d show cell cycle profiles of similar progression of PC3ASL and PC3LacZ cells to the S and $G_2$/M phase up to 6 hours after release, but only the PC3LacZ cells of FIG. 4c continue to the $G_1$ and S phase, whereas the PC3AL cells of FIG. 4d undergo a $G_2$/M arrest from about 10 hours onwards. The reduced expression of LIMK1 in PC3 cells is associated with the suppression of cell growth and cell cycle arrest in the $G_2$/M phase.

FIG. 5a shows transfected cells that were successively induced for from about 46 to about 50 hours before being plated into the invasion chambers. Ectopic expression of LIMK1 in BPH-1 cells increased invasion significantly after induction with ponasterone A, for from about 23 to about 25 hours, with about a 100% difference in invasion in different cell lines. Data represents the mean±S.E. of quantitative analysis of three independent assays (each from two different clones of transfected PC3 and BPH-1 cells).

FIGS. 5b and 5c, are bright field images of cells invaded to the underside of the control and Matrigel membranes.

FIG. 5 d presents staining of LIMK1 in BPHL and BPHLacZ cells showing predominantly cytoplasmic distribution of LIMK1 in BPHL cells. Nuclei were stained with 4,6-diamidino-2-phenylindole at 200× magnification. The Reduced expression of LIMK1 is associated with a reversion of the invasion ability of PC3 cells.

FIGS. 6 a and 6b shows phase-contrast images of PC3LacZ, (FIG. 6a) and PC3ASL cells, (FIG. 6b) after successive induction for 72 h.

FIGS. 6c, 6d, 6e, 6f, 6g and 6h, show dual staining of continuously induced PC3LacZ cells (FIGS. 6c, 6e, and 6g) and PC3ASL cells, (FIGS. 6d, 6f, and 6h) with Alexa 488-conjugated phalloidin and anti-LIMK1, (FIGS. 6c and 6d), anti-paxillin, (FIGS. 6e and 6f,) or MT1-MMP, (FIGS. 6g and 6h) antibodies. Arrows indicate localization of LIMK1 in lamellipodia along with actin in FIG. 6c. Arrows in FIG. 6d indicate accumulation of LIMK1 between actin stress fibers and cell boundary. The arrows in FIG. 6e indicate localization of paxillin to the small adhesion points at the lamellipodia along with actin. The redistribution of paxillin and accumulation in large areas between actin stress fibers and cell periphery is show in FIG. 6f, and localization of MT1-MMP (also in the enlarged section) and actin to the lamellipodia is shown in FIG. 6g. Scale bar, 10 µm.

FIGS. 6i and 6j, indicate phase contrast images of BPHLacZ, 6i and BPHL, 6j showing the difference in growth pattern. Here, reduced expression of LIMK1 is associated with changes in cell morphology, cytoskeleton organization, and the invasive ability of PC3 cells.

DESCRIPTION

Figure 1A:
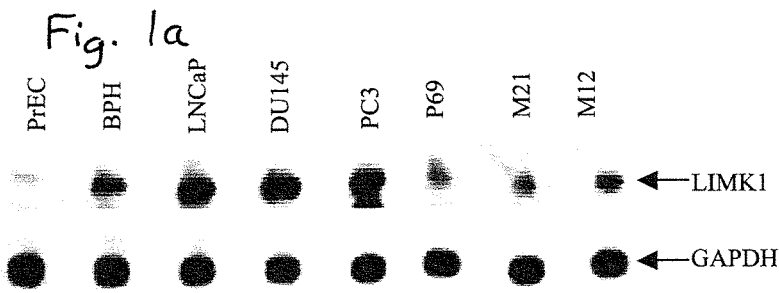
FIG. 1a shows an immunoblot analysis of LIMK1 in total lysates of human prostate cell lines.
Figure 1B:
FIGS. 1b, 1c and 1d show the expression of LIMK1 of normal/benign areas in prostrate tissues.
Figure 1C:
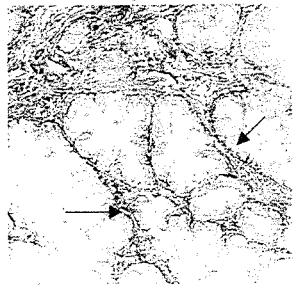
Figure 1D:

Definitions:

The term "actin", as used herein refers to a protein of the myofibril, localized in the I band; acting along with myosin particles, it is responsible for the contraction and relaxation of muscle. In the absence of salt, it becomes globular (G-actin), and in the presence of potassium chloride and adenosine triphosphate it polymerizes, forming long fibers (F-actin).

The term "administer" or "administration" refers to the delivery of a pharmacological composition of the present invention to an individual for the purpose of preventing or treating of a cancer.

The term "antisense RNA", as used herein refers to a single-stranded RNA with a base sequence complementary to a segment of another RNA molecule that can specifically bind to the target RNA and inhibit its activity.

The term "antisense DNA", as used herein refers to a single-stranded DNA with a base sequence complementary to a segment of another DNA molecule that can specifically bind to the target DNA and inhibit its activity.

The term "expression" (gene expression), as used herein refers to the process by which a gene's coded information is converted into the structures present and operating in the cell. Expressed genes include those that are transcribed into RNA but not translated into protein (e.g., transfer and ribosomal RNA's).

The term "nucleic acid", as used herein is defined as family of macromolecules, of molecular masses ranging upward from 25,000, found in the chromosomes, nucleoli, mitochondria, and cytoplasm of all cells, and in viruses; in complexes with proteins, they are called nucleoproteins. On hydrolysis they yield purines, pyrimidines, phosphoric acid, and a pentose, either d-ribose or d-deoxyribose; from the last, the nucleic acids derive their more specific names, ribonucleic acid and deoxyribonucleic acid. Nucleic acids are linear (i.e., unbranched) chains of nucleotides in which the 5-phosphoric group of each one is esterified with the 3-hydroxyl of the adjoining nucleotide.

An "isolated nucleic acid" is a nucleic acid the structure of which is not identical to that of any naturally occurring nucleic acid or to that of any fragment of a naturally occurring genomic nucleic acid spanning more than three separate genes. The term therefore covers, for example, (a) a DNA which has the sequence of part of a naturally occurring genomic DNA molecule but is not flanked by both of the coding sequences that flank that part of the molecule in the genome of the organism in which it naturally occurs; (b) a nucleic acid incorporated into a vector or into the nenomic DNA of a prokaryote or eukaryote in a manner such that the resulting molecule is not identical to any naturally occurring vector or genomic DNA; (c) a separate molecule such as a cDNA, genomic fragment, a fragment produced by polymerase chain reaction (PCR), or a restriction fragment; and (c) a hybrid gene, i.e., a gene encoding a fusion protein. The term "oligonucleotide", as used herein is defined as a molecule comprised of two or more ribonucleotides, and in specific embodiments, more than three ribonucleotides. Its exact size will depend upon many factors which, in turn, depend upon the ultimate function and use of the oligonucleotide.

As used herein, the term "PCR" refers to the polymerase chain reaction that is the subject of U.S. Pat. Nos. 4,683,195 and 4,683,202 to Mullis, as well as other improvements now known in the art.

Two DNA sequences are "substantially homologous" when, for example, at least about 75%, and more specifically, at least from about 90% to about 95% of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system.

The term "vector", as used herein refers to a DNA molecule that replicates on its own in a host cell and can be used as a vehicle in the laboratory for replicating other types of DNA.

Abbreviations used are: LIMK1, LIM kinase 1; NGF, nerve growth factor; EGF, epidermal growth factor; BPH-1, benign prostatic hyperplasia cells.

DESCRIPTION OF THE PREFERRED EMBODIMENTS

Before explaining the disclosed embodiments of the present invention in detail it is to be understood that the invention is not limited in its application to the details of the particular arrangements shown since the invention is capable of other embodiments. Also, the terminology used herein is for the purpose of description and not of limitation.

To understand the role of LIMK1 in prostate cancer, BPH-1, PrEC, LNCaP, DU145, P69, M21, M12, PC3AR, PC3Neo, and PC3 cells were used as models for benign and cancerous prostate cells. The above-mentioned cell lines may be used, for example, in studies on the invasive behavior of prostate cancer, which also exhibited increased expression of LIMK1, as compared with BPH-1. Because the function of LIMK1 is mediated through phosphorylation of cofilin in the reorganization of actin cytoskeleton, the status of the kinase activity of immunoprecipitated LIMK1 from several of the above-mentioned cell lines were studied, which confirmed that the endogenous LIMK1 was catalytically active. Interestingly, a parallel increase in the concentration of endogenous phospho-cofilin was also noted in the cell lines. There was no significant decrease in the concentration of phospho-cofilin after enforced reduction of the expression of LIMK1. Results indicate that antisense-RNA-mediated LIMK1 reduced the expression of LIMK1 and provides evidence of the involvement of LIMK1 in regulation of growth of prostate cancer cells, specifically at the $G_2/M$ phase of the cell cycle.

Results indicate a direct role of LIMK1 in $G_2/M$ phase of the cell cycle, as a partial reduction of LIMK1 expression induced a $G_2/M$ phase arrest, for example, in PC3ASL cells.

Consistent with the effect of LIMK1 in the promotion of cellular invasiveness, a visible alteration in the cell shape and adhesion pattern was caused by a partial reduction in LIMK1 in prostate epithelial cells. In a specific embodiment, PC3ASL cells showed discrete stress fibers, and a more flattened appearance that was typically observed after Rho activation. The effect of LIMK1 in facilitating cell invasion is not mediated through the inactivating phosphorylation of cofilin. This observation suggests a novel area of interaction between LIMK1 and other proteins that are involved in maintenance of cell behavior such as invasion and locomotion. The presence of two LIM domains and a PDZ domain at the amino-terminal end of LIMK1 suggests its possible interaction with other proteins. It has been theorized that the effect of LIMK1 is accomplished through protein-protein interaction, a phenomenon that is sensitive to the stoichiometric balance and can be altered with a partial reduction in LIMK1 concentration. The role of LIMK1 as the regulator of both the $G_2/M$ phase checkpoint and the invasive property of prostate cancer cells and a chromosomal gain on 7q11.2, the region of localization of LIMK1 gene, for example, in metastatic prostate cancer suggests the possibility of LIMK1 as a cellular oncogene. Identification of LIMK1 as a potential promoter of prostate cancer progression may facilitate further characterization of interacting partners involved in progression of primary tumors and metastasis of advanced tumors and provide a novel therapeutic target for prevention of prostate cancer metastasis.

LIM kinase 1 (LIMK1) belongs to a novel dual specificity (serine/threonine and tyrosine) kinase family that contains two amino-terminal LIM domains. The LIMK1 gene is expressed predominantly in brain tissue and developing neural tissue. LIMK1 gene deletion (microdeletion of chromosome 7q11.23) is typical for individuals with Williams's syndrome. Cofilin, a known actin-binding protein is considered to be a potent regulator of actin protein dynamics based upon cofilin's activity in F-actin depolymerization. Cofilin is the only known substrate of LIMK1. The regulatory function of cofilin is inhibited by phosphorylation at the Ser-3 residue by LIMK1, which has been known to lead to an accumulation of F-actin. The catalytic activity of LIMK1 is regulated by distinct members of the Rho protein subfamily of small GTPases (Rho, Rac, and Cdc42), which controls actin filament dynamics and focal adhesion assembly in response to extra- and intracellular stimuli. Rho, Rac, and Cdc42 induce formation of stress fibers, assembly of lamellipodia and membrane ruffles, and the regulation of filopodia) protrusions, respectively. LIMK1 has been shown to mediate specifically Rac-induced actin cytoskeleton reorganization and focal adhesion complexes. Rac-induced activation of LIMK1 is mediated by PAK1, which phosphorylates LIMK1 on its $Thr^{508}$ residue. It has been proposed that Rho and Cdc42-induced cytoskeletal changes are mediated through phosphorylation of LIMK1 by Rho-dependent protein kinase ROCK and Cdc42-regulated protein kinase PAK-4 and MRCKα.

The non-catalytic domain of LIMK1 contains two tandem repeats of a LIM motif, a putative zinc binding motif, and a PDZ domain, which contains two tandem nuclear exit signal sequences. LIMK1 also contains a nuclear localization signal-like basic cluster sequence. The non-catalytic domain of LIMK1 has been shown to effect cytoskeleton reorganization independent of its kinase activity. Specific regions of the non-catalytic domain (LIM or PDZ) inhibit neurite outgrowth in differentiating PC12 cells responding to Ras, neuronal growth factor (NGF) or a ROCK inhibitor without altering endogenous LIMK1 activity. This data suggests that the non-catalytic domain of LIMK1 is involved in regulating cellular processes though protein-protein interaction.

LIMK1 also physically interacts through its LIM domain with the cytoplasmic tail of neuregulins, a family of transmembrane proteins that functions as receptor tyrosine kinase ligands. These proteins are known to be involved in the regulation of synapse formation and maintenance, cell proliferation, apoptosis, differentiation, and neuronal migration. Deletion experiments have shown that the lack of LIM and PDZ domains enhances the effect of LIMK1 on actin cytoskeleton. In addition, expression of a kinase-inactive form of the protein blocked the effect of the native LIMK1. These findings suggest an inhibitory role of the non-catalytic domain in the regulation of the kinase activity associated with LIMK1.

Reorganization of cytoskeleton is an aspect of motility, detachment, and invasion of cancer cells. Individual members of the Rho protein family, such as Rac and Cdc42, induce distinct actin remodeling events, work together at the leading edge of the cell, and coordinate lamellipodia) and filopodial extensions, whereas Rho activates accumulation of stress fibers through activation of ROCK. The formation and stabilization of actin filaments provides the protrusive force for cellular extensions at the leading edge of the migratory cells. These events may affect the invasive behavior of the cancer cells, as the inhibition of Rho kinase activity has been shown to reduce the invasive progress of prostate cancer cells in vivo. Rho proteins are activated by growth factor receptors and their ligands, for example, EGF and NGF and their respective receptors erbB2 and Trk. Cellular-erbB2 and Trk are often over expressed and activated in various types of cancers including prostate, lung, breast, and ovarian cancers. Furthermore, c-erbB2 was shown to enhance the invasiveness and metastatic potential of cancer cells. Similarly, NGF and Trk expressions in prostate cancer cells coincide with transformation to a malignant phenotype capable of invading the perineural space and extra capsular metastasis to a distant site. As evident from membrane ruffling and lamellipodia formation, EGF- and NGF-induced invasion of prostate tumor cells is mediated through Rac. It is likely that Rac-mediated activation of actin reorganization is mediated through LIMK1. cDNA microarray and differential display reverse-transcription PCR analyses indicate over expression of LIMK1 mRNA and LIMK1 as the elastin-linked gene in prostate adenocarcinoma cells. Experimental data indicates that LIMK1 is over expressed in prostate adnocarcinomatous tissues and in malignant prostate cell lines and may be necessary for the invasive property and growth of prostate cancer cells. This effect is not mediated through the inactivation of the phosphorylation of cofilin.

Recent studies show that LIMK1 undergoes mitosis-specific activation by hyperphosphorylation, which is associated with a concomitant increase in phosphorylation of cofilin. LIMK1 becomes activated in prometaphase and metaphase and comes back to the basal level as cells enter telophase, which suggests that a controlled activity of cofilin by phosphorylation and dephosphorylation is necessary for mitosis.

A direct role of LIMK1 in promoting cellular invasion, a hallmark of metastasis, is evident based on Matrigel-based invasion assay analysis. A partial inhibition of LIMK1 reduced the percentage of invading cells down to the level observed for BPH-1 cells. However, the effect of ectopic expression with regards to LIMK1 in BPH-1 cells on the promotion of the invasion was more pronounced and significantly higher than the highly metastatic PC3 cells, suggesting a possible role for LIMK1 in the acquisition of metastatic behavior of prostate tumors. An increased expression of LIMK1 in metastatic prostate tumors, may indicate an association of LIMK1 expression with advanced prostate cancer. It is possible that the effect of growth factors on the increased invasion is mediated through LIMK1 in advanced prostate cancer in which specific receptors for NGF and EGF are over expressed. However, it is unclear how the ectopic expression of LIMK1 promotes cellular invasion in BPH-1 cells, in which the upstream effectors of LIMK1 may not be activated without specific extra-cellular signals.

Mammalian LIM kinase 1 is involved in the reorganization of the actin cytoskeleton through the inactivating phosphorylation of the ADF family protein cofilin that depolymerizes actin filaments. Maintenance of actin dynamics in an ordered fashion is required for the stabilization of cell shape and for the promotion of cell motility of some cell types. Cell shape and promotion of cell motility are two phenomena that may become altered during acquisition of the metastatic phenotype by the cancer cell. Data indicates that when LIMK1 is over-expressed in mammalian prostate tumors and prostate cancer cells, the concentration of phosphorylated cofilin is higher in metastatic prostate cancer cells.

Antisense agents are tools for use in inhibiting the expression of target genes in a sequence-specific manner and have found use in functional genomics, target validation, and for therapeutic purposes. Different types of anti-mRNA strategies, for example, the use of single stranded antisense-oligonucleotides, the triggering of RNA cleavage through catalytically active oligonucleotides referred to as ribozymes, and RNA interference induced by small interfering RNA molecules, have been attempted. The successful use of antisense agents may depend, for example, on identifying accessible sites of the target RNA for oligonucleotide binding, protecting the antisense agents from nucleolytic attack, preventing their cellular uptake, and providing for the correct intracellular localization. Some success has been shown with chemically modified nucleotides, for example, alkyl modifications at the 2' position of the ribose. These chemically modified nucleotides have shown improved serum stability, higher target affinity and low toxicity. In addition, RNA-cleaving ribozymes and deoxy-ribozymes, along with the use of 21-mer double-stranded RNA molecules for RNA interference applications in mammalian cells has shown efficiency in the suppression of the expression of specific genes.

Antisense approaches differ from conventional drugs, most of which bind to proteins and thereby modulate their function. In contrast, antisense agents act at the mRNA level, preventing its translation into protein. Antisense-oligonucleotides (AS-ONs) pair with their complementary mRNA, whereas ribozymes and DNA enzymes are catalytically active oligonucleotides that not only bind, but can also cleave, their target RNA. Recently, progress that been made with the development and use of chemically modified nucleotides that stabilize oligonucleotides against nucleolytic degradation and enhance their target affinity. In addition RNA interference may be used as an efficient method of suppressing gene expression in mammalian cells by the use of 21-23 mer small interfering RNA (siRNA) molecules.

Antisense-oligonucleotides combine many desired properties, for example, broad applicability, direct utilization of sequence information, rapid development at low costs, high probability of success and high specificity compared to alternative technologies for gene functionalization and targeting. Antisense oligonucleotides have also proved useful in animal models for therapeutic purposes.

Antisense-oligonucleotides may, for example, consist of from about 15 to about 20 nucleotides, which are complementary to their target mRNA. Phosphorothioate (PS) oligodeoxynucleotides are one type of oligonucleotide used for inhibiting gene expression. In this class of oligonucleotide, one of the non-bridging oxygen atoms in the phophodiester bond is replaced by sulfur. The introduction of phosphorothioate linkages into oligonucleotides was primarily intended to enhance their nuclease resistance. Phosphorothioate DNAs have a half-life in human serum of from about 9 to about 10 hours compared to about 1 hour for unmodified oligodeoxynucleotides. In addition to nuclease resistance, phosphorothioate DNAs form regular Watson-Crick base pairs, activate RNase H, carry negative charges for cell delivery and display attractive pharmacokinetic properties.

Another class of antisense oligonucleotides contains alkyl modifications at the 2' position of the ribose. 2'-O-methyl and 2'-O-methoxy-ethyl RNA are members of this class. 2'-O-alky RNA oligonucleotides do not recruit RNase H, their antisense effect is due, for example, to a steric block of translation. Other antisense oligonucleotides modifications may include, for example, C-5 propyne, 2'-O-aminopropyl, and dipyridophenazine-DPPZ A chemically synthesized antisense nucleic acid molecule or ribozyme may be introduced into a cell by any of a variety of methods know in the art (Sambrook et al., supra, 1989, and in Ausubel et al., Current Protocols in Molecular Biology, Hohn Wiley and Sones, Baltimore, Md. (1994), incorporated herein by reference in its entirety), including, for example, transfection, microinjection, electroporation or the use of liposomes. In addition, it is recognized by those skilled in the art that naked nucleic acid molecules are taken up by cells in vivo and, therefore, the antisense nucleic acid molecule of the invention may be administered, for example, directly to the region containing the cancer cells. More specifically, antisense nucleic acid molecules may be introduced into a cell using methods that do not require the initial introduction of an encoding nucleic acid molecule into a vector. For example, a nucleic acid molecule encoding an antisense LIMK1 molecule can be introduced into a cell using a cationic liposome, which also can be modified with specific receptors or ligands as described above (Morishita et al., J. Clin. Invest., 91:2580-2585 (1993), incorporated herein by reference; see, also, Nabel et al., supra, 1993)). In addition, a nucleic acid molecule may be introduced into a cell using adenovirus-polylysine DNA complexes (see, for example, Michael et al., J. Biol. Chem., 268:6866-6869 (1993), and incorporated herein by reference in its entirety).

Embodiments of the present invention also includes nucleic acids that hybridize under stringent hybridization conditions, as defined herein, to all or a portion of the nucleotide sequence represented by SEQ ID NO: 1 or its complement. The hybridizing portion of the hybridizing nucleic acid varies from about 80%, and for example, at least 95%, or at least 98% identical to the sequence of a portion or all of a nucleic acid encoding a polypeptide, or its complement. Hybridizing nucleic acids of the type described herein can be used, for example, as a cloning probe, a primer (e.g, a PCR primer), or a diagnostic probe. Hybridization of the oligonucleotide probe to a nucleic acid sample typically is performed under stringent conditions. Nucleic acid duplex or hybrid stability is expressed as the melting temperature or Tm, which is the temperature at which a probe dissociates from a target DNA. This melting temperature is used to define the required stringency conditions. If sequences are to be identified that are related and substantially identical to the probe, rather than identical, then it is useful to first establish the lowest temperature at which only homologous hybridization occurs with a particular concentration of salt (e.g., SSC or SSPE).

Then, assuming that 1% mismatching results in a 1° C. decrease in the Tm, the temperature of the final wash in the hybridization reaction is reduced accordingly (for example, if sequences having >95% identity with the probe are sought, the final wash temperature is decreased by 5° C.). In practice, the change in Tm can be from about 0.5° C. to about 1.5° C. per 1% mismatch. Stringent conditions involve hybridizing at about 68° C. in 5×SSC/5×Denhardt's solution/1.0% SDS, and washing in 0.2×SSC/0.1% SDS at about 37° C. Moderately stringent conditions include washing in 3×SSC at about 42° C. The parameters of salt concentration and temperature can be varied to achieve the optimal level of identity between the probe and the target nucleic acid. Additional guidance regarding such condition parameters are readily available in the art, for example, by Sambrook et al., 1989, Molecular Cloning, A Laboratory Manual, Cold Spring Harbor Press, N.Y.; and Ausubel et al. (eds.), 1995, Current Protocols in Molecular Biology, (John Wiley & Sons, N.Y.) at Unit 2.10, both of which are incorporated herein by reference in their entirety.

Any individual domain, for example, an LIM, a PDZ, or a LIM kinase domain, individually or in combination, may be used and/or modified while retaining the activity of the polypeptide.

As used herein, "percent homology" of two amino acid sequences or of two nucleic acids may be determined using the algorithm of Karlin and Altschul (Proc. Natl. Acad. Sci. USA 87:2264-2268, 1990), modified as in Karlin and Altschul (Proc. Natl. Acad. Sci. USA 90:5873-5877, 1993), both of which are incorporated herein by reference in their entirety. Such an algorithm is incorporated into the NBLAST and XBLAST programs of Altschul et al. (J. Mol. Biol. 215:403-410, 1990), incorporated herein by reference in its entirety. BLAST nucleotide searches are performed with the NBLAST program, score=100, word length=12, to obtain nucleotide sequences homologous to a nucleic acid molecule of the invention. BLAST protein searches are performed with the XBLAST program, score=50, word length=3, to obtain amino acid sequences homologous to a reference polypeptide (e.g., SEQ ID NO: 2). To obtain gapped alignments for comparison purposes, Gapped BLAST is utilized as described in Altschul et al. (Nucleic Acids Res. 25:3389-3402, 1997), incorporated herein in its entirety. When utilizing BLAST and Gapped BLAST programs, the default parameters of the respective programs (e.g., XBLAST and NBLAST) are used. See http://www.ncbi.nlm.nih.gov.

Such a composition typically contains from about 0.1 to about 90% by weight (such as 1 to 20% or 1 to 10%) of a therapeutic agent of the invention in a pharmaceutically acceptable carrier. Solid formulations of the composition for administration may contain suitable carriers or excipients, such as corn starch, gelatin, lactose, acacia, sucrose, microcrystalline cellulose, kaolin, mannitol, dicalcium phosphate, calcium carbonate, sodium chloride, or alginic acid. Disintegrators that can be used include, without limitation, microcrystalline cellulose, corn starch, sodium starch lycolate and alginic acid. Lubricants that may be used include magnesium stearates, stearic acid, silicone fluid, talc, waxes, oils, and colloidal silica.

Injectable formulations of the compositions may contain various carriers such as vegetable oils, dimethylacetamide, dimethylformamide, ethyl lactate, ethyl carbonate, isopropyl myristate, ethanol, polyols (glycerol, propylene glycol, liquid polyethylene glycol, and the like). For intravenous injections, water soluble versions of the compositions may be administered by the drip method, whereby a pharmaceutical formulation containing an antifungal agent and a physiologically acceptable excipient is infused. Physiologically acceptable excipients may include, for example, 5% dextrose, 0.9% saline, Ringer's solution or other suitable excipients. Intramuscular preparations, e.g., a sterile formulation of a suitable soluble salt form of the compositions, can be dissolved and administered in a pharmaceutical excipient such as Water-for-Injection, 0.9% saline, or 5% glucose solution. A suitable insoluble form of the compositions may be prepared and administered as a suspension in an aqueous base or a pharmaceutically acceptable oil base, such as an ester of a long chain fatty acid (e.g., ethyl oleate).

A topical semi-solid ointment formulation typically contains a concentration of the active ingredient from about 1 to about 20%, e.g., 5 to 10%, in a carrier such as a pharmaceutical cream base. Various formulations of topical use include drops, tinctures, lotions, creams, solutions and ointments containing the active ingredient and various supports and vehicles. The optimal percentage of the therapeutic agent in each pharmaceutical formulation varies according to the formulation itself and the therapeutic effect desired in the specific pathologies and correlated therapeutic regimens.

Conventional methods, known to those of ordinary skill in the art of medicine, can be used to administer the pharmaceutical formulations(s) to the patient. For example, any known viral vector or any known method for delivering RNA to prostate cells may be used. Typically, the pharmaceutical formulation will be administered to the patient by applying to the skin of the patient a transdermal patch containing the pharmaceutical formulation, and leaving the patch in contact with the patient's skin generally for from about 1 to about 5 hours per patch. Other transdermal routes of administration (e.g., through use of a topically applied cream, ointment, or the like) can be used by applying conventional techniques. The pharmaceutical formulation(s) can also be administered via other conventional routes (e.g., oral, subcutaneous, intrapulmonary, transmucosal, intraperitoneal, intrauterine, sublingual, intrathecal, or intramuscular routes) by using standard methods. In addition, the pharmaceutical formulations can be administered to the patient via injectable depot routes of administration such as by using 1-, 3-, or 6-month depot injectable or biodegradable materials and methods.

Regardless of the route of administration, the therapeutic agent typically is administered at a daily dosage of from about 0.01 mg/kg to about 30 mg/kg of body weight of the patient, for example, from about 1 mg/kg to about 5 mg/kg. The pharmaceutical formulation can be administered in multiple doses per day, if desired, to achieve the total desired daily dose.

The effectiveness of the method of treatment can be assessed by monitoring the patient. For example, a decrease in the spread or proliferation of prostate cancer cells can be detected by monitoring the patient for a dose-dependent reduction in prostate-specific antigen (PSA) levels. Dose-dependent reductions in PSA correlate with a dose-dependent decrease in the spread of prostate cancer cells.

There are several techniques and methods known in the art for in vivo identification and monitoring of cancer cell metastasis. For example, bone scintigraphy may be used in monitoring. Prostate specific membrane antigen (PSMA) scintigraphy, is known and is one of the most sensitive imaging techniques for the initial detection of bone metastases and is widely used in the staging of prostatic cancer. PSMA is found in normal prostatic epithelial cells and is elevated in prostate cancers, especially in poorly differentiated, metastatic, and hormone refractory carcinomas. Tumor scintigraphy may be used for, but is not limited to, detection of certain primary, metastatic, and recurrent tumors, evaluation of abnormal imaging and non-imaging findings in patients with a history of certain tumors, and reassessment of patients for residual tumor burden after therapy. Bone is the most common site of circulatory (or haematogenous) metastases from prostate cancer. Bony metastases are found in 85% of patients dying of the disease. Radionuclide scintigraphy using a radioactively labeled chemical is administered to the patient and is taken up in areas of increased bone turnover or growth. Although sensitive, this technique is not specific and false-positives may be obtained in cases of recent bone trauma, degenerative joint disease or Paget's disease. Other imaging techniques include single photon emission computed tomography (SPECT), positron emission tomography (PET), computed tomography (CT), magnetic resonance imaging (MRI), and magnetic resonance spectroscopy (MRS). ProstaScint Imaging is based on using planar and SPECT imaging to map the uptake of capromab pendetide that has been labeled with a radionucliotide. Capromab pendetide is a monoclonal antibody that targets prostate-specific membrane antigen, a transmembrane glycoprotein that has been thoroughly characterized because of its role as a marker for prostate cancer and metastases. As with all scintigraphic studies, correlation of findings with results of other imaging and non-imaging modalities, as well as with clinical information, is necessary for maximum diagnostic yield.

Prostate Specific Antigen (PSA) measurements are known in the art and have been shown to be accurate and cost-effective predictors of prostate cancer cell proliferation.

In one embodiment the composition may, for example, be presented in a pack or dispenser device, such as an FDA approved kit, which may contain one or more unit dosage forms of the active ingredient. The pack may, for example comprise metal or plastic foil. The pack or dispenser device may be accompanied by instructions for administration.

EXAMPLE 1

Cell Culture, Transfection, and Isolation of Stable Cell Line

The following cell lines, including, PC3, DU145, LNCaP, PrEC, Benign Prostatic Hyperplasia (BPH-1), P69, M21, and M12 were maintained in RPMI (DU145, LNCaP, P69, M21, and M12), Ham-12 (PC3), DMEM (BPH-1) and in the specific medium (PrEC) and grown to log phase before being used. PC3 cells were transfected using LipofectAMINE™ with the open reading frame of the LacZ gene or the antisense cDNA of the coding sequence of LIMK1 (1.94 kilobases), both cloned into an ecdysoneinducible mammalian expression vector pIND. BPH-1 cells (benign prostatic hyperplasia) were transfected with the open reading frames of LIMK1 or LacZ cloned in pIND. Cells were cotransfected with the vector pVRxR that encodes the subunit of a heterodimer of the ecdysone and the retinoid X receptor to establish stable cell lines (PC3ASL and PC3LacZ) capable of expressing antisense LIMK1 RNA or LacZ when induced with an ecdysone analogue, ponasterone A. Double stable clones were selected using from about 450 µg/ml to about 550 µg/ml Geneticin™ and from about 45 µg/ml to about 55 µg/ml Zeocin™. Stable transfected cells were continuously induced by adding from about 4 µM to about 6 µM ponasterone A for from about 20 to about 24 hours.

EXAMPLE 2

Immunoblotting, Immunohistochemistry, and Immunofluorescence

Total cell lysates were resolved in a from about 10 to about a 14% solution of SDS-PAGE and subjected to immunoblotting using anti-LIMK1, anti-cofilin, or anti-phospho-cofilin antibodies. Anti-glyceraldehyde-3-phosphate dehydrogenase antibody was simultaneously used as an internal control. Goat anti-mouse or anti-rabbit antibody was used as the secondary antibody. Paraffin-embedded tissue sections of normal and malignant human prostate were subjected to a pepsin-based antigen retrieval protocol followed by incubation with anti-LIMK1 antibody. A biotinylated multi-link goat anti-immunoglobulin for mouse, rabbit, guinea pig, and rat was used as the secondary antibody. Positive signals were detected by horseradish peroxidase-conjugated streptavidin and 3,3'-diaminobenzidine (DAB) as the chromogen. For indirect immunofluorescence, PC3ASL and PC3LacZ cells were plated on poly-L-lysine-coated glass cover slips and continuously induced for from about 70 to about 74 hours. Cells were permeabilized and dually stained with Alexa Fluor 488-conjugated phalloidin and anti-LIMK1, anti-paxillin, or anti-MT1-MMP antibodies. Cy3-conjugated anti-mouse or anti-rabbit antibody (Molecular Probes) was used as the secondary antibody. Fluorescent images were captured using a laser-scanning confocal microscope.

EXAMPLE 3

In Vivo Phosphorylation, Expression of Recombinant Protein, and Immunecomplex Kinase Assay BPH-1 and PC3 cells were cultured in the presence of 1.5 mCi of [32P]orthophosphate forr from about 10 hours. Equal amounts of total cell lysates were subjected to immunoprecipitation with anti-cofilin antibody and protein A-agarose beads (Sigma) using the procedure as described, and the products were resolved in a from about a 10 to about a 14% solution of SDS-PAGE. Labeled cofilin was detected by autoradiography and PhosphorImager analysis. Recombinant cofilin was expressed in *Escherichia coli* as a His-tagged fusion protein by cloning the open reading frame of human cofilin into the T7 polymerase driven pET30Ek/LIC (Novagen) expression vector using specific primers (F, 5'-GACGACGACAAGATGGCCTCCGGTGTGGCTG-3' (SEQ ID NO. 2), and R, 5'-GAGGAGAAGCCC GGTTCA-CAAAGGCTTGCCC-3',(SEQ ID NO. 3)). The expression construct was used to transform BL21 (DE3) *E. coli* cells. Transformed cells were induced with 1 mM isopropyl-1-thio-β-D-galactopyranoside at 25° C., and the expressed cofilin was purified through a Nickel affinity column.

EXAMPLE 4

For immune complex kinase assay, LIMK1 was immunoprecipitated from PC3 cells cultured under regular conditions using anti-LIMK1 antibody and protein G-agarose (Sigma) beads. Protein G-agarose beads bound to the immune complex were re-suspended in kinase assay buffer comprising from about 45 to about 55 mM HEPES, a pH of from about 7.0 to about 8.0, from about 100 to about 200 mM NaCl, from about 45 to about 55 µM ATP, from about 4 to about 6 mM $MgCl_2$, from about 4 to about 6 mM $MnCl_2$, from about 9 to about 11 mM NaF, from about 0.5 to about 1.5 mM $Na_3VO_4$, from about 2 to about 4 nM [$\gamma$-$^{32}$P]ATP) and incubated at about 30° C. for from about 15 to about 25 minutes with from about 9 to about 11 µg of recombinant cofilin as the substrate. The reaction mixture was resolved in a from about 12% to about a 16% solution of SDS-PAGE, and phosphorylated cofilin was detected by autoradiography and PhosphorImager analysis.

EXAMPLE 5

Invasion Assay

Cells were plated in serum-free media (containing ponasterone A for transfected cells) as a control and Matrigel-coated membrane containing invasion chambers. Cells were incubated at about 37° C. for from about 20 to about 24 hours in a $CO_2$ incubator using from about a 4 to about a 6% fetal bovine serum in the lower chamber as the chemoattractant. Invading cells were stained with Diff-Quick™ stain and counted. The percentage of metastasizing cells that invaded through the Matrigel-coated membranes was calculated by comparison with the cells passed through the membranes in the control chambers. The results are shown in FIG. 5.

EXAMPLE 6

[$^3$H]Thymidine Incorporation, Cell Synchronization, and Fluorescence-Activated Cell Sorter Analysis Asynchronous PC3LacZ and PCASL cells were incubated with about 1 µCi of [$^3$H]thymidine in the presence or absence of ponasterone A. At about 10 minute time intervals after induction, cells were treated with a 5% trichloroacetic acid solution and lysed using a 0.5 N NaOH solution. Incorporation of [$^3$H]thymidine to DNA was measured in a scintillation counter (Beckman LS 5000 TD). For cell cycle analysis, PC3LacZ and PC3ASL cells induced at from about every 20 to about every 24 hours, were synchronized at the $G_1$/S phase boundary by a double thymidine block by treating them with a solution of from about 1 to about 3 mM thymidine for from about 22 to about 26 hours followed by a release of from about 7 to about 9 hours in fresh growth medium and successive re-treatment with thymidine (2 mM) for about 16 hours. The cells were then released to enter the cell cycle in fresh growth medium and harvested at specified time intervals. The cells were fixed in a solution of from about 0.5 to about 1.5% paraformaldehyde in phosphate-buffered saline (PBS), washed in PBS, permeabilized with a solution of from about 0.2% to about 0.3% saponin in PBS, and treated with from about 0.5 mg/ml to about 1.5 mg/ml of a solution of RNase (1 mg/ml) at from about 37° C. The cells were washed in phosphate-buffered saline and stained with a from about 350 to about a 450 µg/ml solution of propidium iodide at about 37° C. for from about 25 to about 35 minutes. The cells were analyzed in a flow cytometer, and the raw data was analyzed using Modfit (BD Biosciences) software.

EXAMPLE 7

Figure 1E:
FIGS. 1e, 1f, and 1g show the expression of LIMK1 of cancerous glands in prostrate tissues.
Figure 1F:
Figure 1G:
Figure 4A:
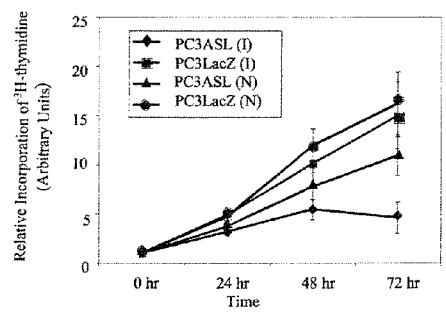
FIG. 4a depicts a [$^3$H]thymidine incorporation in PC3ASL and PC3LacZ cells induced successively (I) or not (N). Data represents values relative to the initial time point (0 hours) and as the mean±S.E of three independent experiments.
Figure 4B:
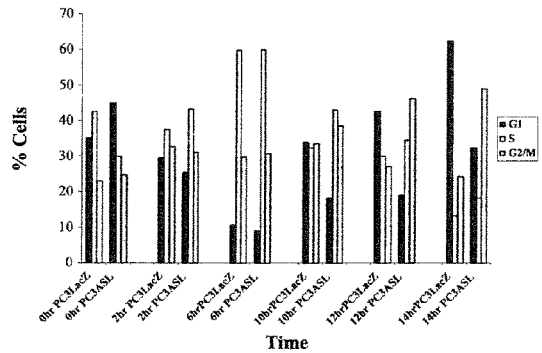
FIGS. 4b, 4c, 4d shows the flow cytometric analysis of cell cycle transition in synchronized PC3LacZ (FIG. 4c) and PC3ASL (FIG. 4d) cells successively induced for 72 hours. Cells were arrested at the $G_1$/S phase boundary and released.
Figure 4C:
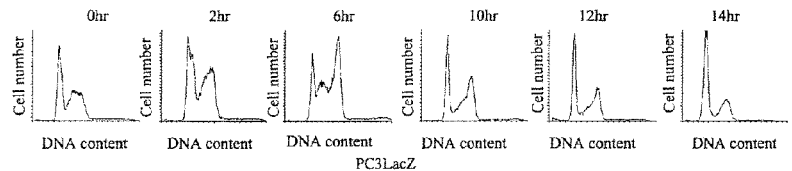
Figure 4D:
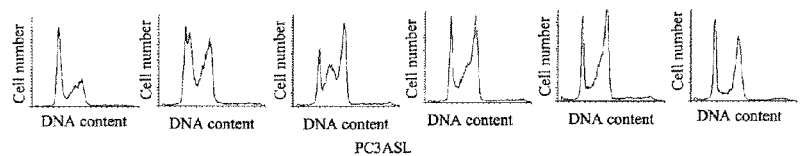

LIMK1 is Over Expressed in Cancerous Prostate Cells and Tissues and is Catalytically Active To confirm the differences in the expression of LIMK1 in prostate cancer, the expression profile of LIMK1 was monitored in various prostate cell lines, for example, DU145, LNCaP, PrEC, Benign Prostatic Hyperplasia (BPH-1), P69, M21, and M12 were maintained in RPMI (DU145, LNCaP, P69, M21, and M12), Ham-12 (PC3), DMEM (BPH-1) and prostate tissues. Results of the monitoring indicated an increased expression of LIMK1 in aggressive metastatic prostate epithelial cells and in some prostatic adenocarcinomas (FIG. 1). The concentration of LIMK1 in some cancerous prostate cell lines (M21 and M12) increased proportionately with increasing tumorigenic and aggressive properties when compared with normal prostate epithelial cells, P69 and BPH-1 cells (FIG. 1a). An increase of from about 200% to about 300% expression of LIMK1 was noted in tumorigenic cells, LNCaP, M21 and metastatic cells, PC3, DU145, and M12 prostate cancer cells when compared with BPH-1 and P69 (non-tumorigenic) cells (FIG. 1a). Compared with prostate epithelial cells, the expression of LIMK1 was, for example, from about 500% to about 1000% higher in the metastatic prostate cancer cells, PC3 and M21 (FIG. 1a). Consistent with these findings, immunohistochemical analysis indicated a higher expression of LIMK1 in some cancerous glands in prostatic epithelium (FIGS. 1e, f, and g). The expression of LIMK1 in prostate tissues was localized to the basal cells in benign glands (arrows in FIGS. 1b, c and d) compared with a widespread expression and staining in both the cytoplasm and the nucleus in the epithelial cells of cancerous glands (arrows in FIGS. 1e, f, and g). These results indicate a correlation between over expression of LIMK1 and phenotypic differences in prostate tissues.

The expressed LIMK1 in prostate cancer cells was catalytically competent because immunoprecipitated LIMK1 (FIG. 2, a and b) from PC3 cells was capable of phosphorylating recombinant cofilin (FIG. 2c), the only known substrate of LIMK1. To determine whether the increased expression of LIMK1 was associated with an increased phosphorylation of endogenous cofilin, the phosphorylation status of the native cofilin in BPH-1 and PC3 cells was studied using in vivo phosphorylation and immunoblotting techniques. Although no significant difference in the expression of cofilin was noted in these two cell lines an increase of from about 60% to about 80% in the phosphorylated cofilin was noted in the PC3 cells (FIG. 2, d and e), which demonstrates a parallel increase in phosphorylated cofilin within these cells.

EXAMPLE 8

A Partial Inhibition of LIMK1 Expression Did not Result in Reduced Phosphorylation of Cofilin To understand the possible role of over expressed LIMK1 in the acquisition of tumorigenic and metastatic phenotypes, antisense-RNA mediated functional inactivation of LIMK1 was used; subsequently, a PC3ASL cell line was generated which was capable of expressing antisense LIMK1 RNA after induction with an ecdysone analogue, ponasterone A. A time course study using PC3ASL cells and a control transformed cell line, PC3LacZ, after continuous induction for from about 20 to about 22 hours for a total of 72 hours, indicated the maximum expression of LIMK1 antisense transcript at about 72 hours, which was associated with a concurrent decrease in the concentration of the sense LIMK1 transcript only in the induced PC3ASL cells (FIG. 3a). No decrease in the LIMK1 transcript was apparent in any of the PC3LacZ cells induced or not or in un-induced PC3ASL cells (FIG. 3, a and b). A parallel reduction in the LIMK1 protein concentration confirmed the decreased synthesis of LIMK1 in PC3ASL cells (FIG. 3c). Immunoblot analysis using anti-cofilin or antiphospho-cofilin antibodies revealed no simultaneous decrease in the concentration of phosphorylated cofilin in PC3ASL cells (FIG. 3d). This observation suggests, for example, that, the residual LIMK1 can be catalytically more efficient and maintain an increased concentration of phosphorylated cofilin or the enhanced phosphorylation of cofilin was not mediated by LIMK1. Although cofilin is the only known substrate of LIMK1, it can be phosphorylated by other serine/threonine kinases, such as LIMK2 and TESK1/TESK2.

EXAMPLE 9

Reduced Expression of LIMK1 Retarded Cell Proliferation by Arresting Cells at the $G_2/M$ Phase of the Cell Cycle The effect of a reduced expression of LIMK1 with regard to cell proliferation and cell cycle progression was studied. LIMK1 is expressed in a growth phase-dependent manner, which suggests, for example, its possible involvement in the regulation of cell growth.

The growth pattern of induced and non-induced PC3ASL and PC3LacZ cells by [$^3$H]thymidine incorporation assay was monitored. Results indicated that the inhibition of expression of LIMK1 led to a block in [$^3$H]thymidine incorporation only in PC3ASL cells after about 48 hours of continuous induction (FIG. 4a), signifying a growth arrest in PC3ASL cells. A possible role, for example, of active LIMK1 in regulating mitosis has been suggested also, based on the studies that have shown that the LIMK1 activity fluctuates with cell cycle progression and attains a maximum level during mitosis when LIMK1 becomes hyperphosphorylated, presumably by mitotic Cdks. Induced PC3ASL and PC3LacZ cells synchronized at the $G_1/S$ phase boundary by double thymidine block were used and the cell cycle progression was monitored by harvesting cells at different time points after the release of the block. At about 0 hours, from about 75 to about 78% of the PC3ASL and PC3LacZ cells had progressed to the $G_1/S$ phase of the cell cycle. The remaining from about 22% to about 25% of cells had progressed to the $G_2/M$ phase of the cell cycle, as determined by the higher DNA content in a subpopulation of PC3 cells with inherent chromosomal gain. After the release of thymidine block, both cell types exhibited progression through the S phase, about 60% of the cells and for the $G_2/M$ phase, about 30% of the cells during the next 6 hours. PC3LacZ cells cycled through the $G_1$ phase as a gradual increase in the percent of cells in the $G_1$ phase was noted with a concurrent decrease in the total percent of cells in the S and $G_2/M$ phases from about the $6^{th}$ to about the 14th hours (FIG. 4, b and c). In contrast, the PC3ASL cells started to accumulate in the $G_2/M$ phase during this time with about 50% of the cells at 14 hours, indicating a $G_2/M$ phase arrest in these cells (FIG. 4, b and d). The absence of any blockage in the cell cycle progression of the PC3LacZ cells (FIG. 4, b and c) confirms that a threshold concentration of LIMK1 is necessary for the passage of cells through the $G_2/M$ phase of the cell cycle. These results are also consistent with the [$^3$H] thymidine incorporation data, indicating a growth arrest in the PC3ASL cells.

EXAMPLE 10

Reduced Expression of LIMK1 Abolished the Invasive Behavior of Prostate Cancer Cells The inhibition of LIMK1 expression on the invasive property of PC3 cells was studied using an in vitro invasion assay. The untransfected PC3 cells indicated that a from about 200% to about a 300% increase of the untransfected PC3 cells were invasive and migrated through the Matrigel compared with the non-invasive BPH-1 cells (FIG. 5, a and b). A partial inhibition of LIMK1 expression in PC3ASL cells resulted in a from about 350 to about 550% decrease in the percent of invaded cells compared with wild type PC3 and PC3LacZ cells (transfection control). This was comparable to the percent of BPH-1 cells invaded through the membranes. Results, as shown in FIG. 3, confirm that LIMK1 is necessary to carry out the invasive function of PC3 cells.

EXAMPLE 11

The effect of the ectopic expression of LIMK1 and LacZ, as the control in non-invasive BPH-1 cells was studied in an effort to confirm the role of LIMK1 in promoting invasiveness of prostate epithelial cells. Expression of LIMK1 in transfected BPH-1 cells after induction by ponasterone A showed predominantly cytoplasmic localization of LIMK1 (FIG. 5d) and altered the growth pattern from a clustered and patchy appearance (BPHLacZ)) to a more uniform distribution of single cells (BPHL) (FIG. 6, i and j). Expression of LIMK1 in ponasterone A-treated BPHL cells increased by 1300% the percentage of invasive cells when compared with BPH-1 cells expressing LacZ (FIG. 5, a and c). This suggests the acquisition of a new invasive phenotype by the non-invasive prostate cells. Results provided evidence that LIMK1 may be one of the key proteins that promotes invasiveness and indicates that the increased expression of LIMK1 in PC3 cells may render them metastatic.

EXAMPLE 12

Altered Expression of LIMK1 Changes Cell Morphology and Organization of Actin Cytoskeleton The dynamic regulation of the actin cytoskeleton and the extra-cellular matrix degradation are both required for the invasion process of tumor cells to progress. Reductions in these processes following the reduced expression of LIMK1 in PC3 cells was monitored. The induced PC3LacZ cells exhibited cell morphology typically observed in PC3 cells, with smooth edges and the occasional presence of the filopodial spike-like structures extended from one or both ends of the cell and, in some cases, a phase dense border, characteristic of ruffling lamellipodia around an extensive area of the cell periphery (FIG. 6a, arrows). From about 70 to about 90% of the induced PC3ASL cells, however, showed a more flattened and irregular shape, with several dark patches at the periphery of the cells (arrows in FIG. 6b) that appear to be possible adhesion points. Fluorescent staining of actin cytoskeleton indicated a prominent actin meshwork, characteristic of lamellipodia formation at the leading edge of the induced PC3LacZ cells (FIG. 6c, middle and right); this meshwork was also typical of parental PC3 cells (data not shown) and of motile cells. Immunolocalization of LIMK1 (FIG. 6c) showed a perinuclear distribution, with distinct targeting to the ruffles at the leading edge of these cells (arrows in FIG. 6c, left). In contrast, from about 70 to about 90% of induced PC3ASL cells showed a predominant formation of discrete stress fibers and focal adhesions typically observed in non-motile adherent cells (FIG. 6d, middle and right). Distribution of LIMK1 in these cells was also perinuclear, with one or more broad areas of accumulation (arrows) at the periphery of the cell (FIG. 6d, left).

Changes in the adhesion system of the PC3ASL and PC3LacZ cells were investigated by monitoring immunolocalization of paxillin, an adapter protein associated with focal adhesions of adherent cells (FIG. 6e). PC3LacZ cells showed the presence of paxillin as broad areas surrounding the nucleus and small adhesion sites at the cell periphery, which overlapped the actin meshwork that forms the lamellipodia (arrows in FIG. 6e, left, middle, and right). In contrast, paxillin was more centrally localized in PC3ASL cells, with frequent accumulation in broad areas between the actin meshwork (arrows) representative of stress fibers (FIG. 6f; left, middle, and right) and the cell boundary.

Published reports indicate an elevated expression of the membrane-type matrix metalloproteinase MT1-MMP in invasive prostate cancer cells such as PC3 and DU145. Because the localization of MT1-MMP to lamellipodia has been correlated with the invasive properties of cells, the distribution of this protein in PC3ASL and PC3LacZ cells was monitored. Distribution of MT1-MMP in induced PC3LacZ was localized to the perinuclear and to the lamellipodia along with actin (arrows in FIG. 6g, left, middle, and right) but mainly in the perinuclear region in PC3ASL cells (FIG. 6h) and between actin stress fibers (enlarged box). These results indicate that a reduction in LIMK1 concentration induced beneficial changes in the actin cytoskeleton reorganization, the adhesion pattern, and localization of MT1-MMP in PC3 cells.

An increase in the expression of LIMK1 showed a correlation with the aggressiveness of metastasizing cancer cells. For example, expression of LIMK1 was higher in metastatic PC3 cells and M12 cells when compared with the less-aggressive LNCaP and M21 cells. Consistent with this observation, expression of LIMK1 was significantly higher in cancerous prostate tissues compared with histologically normal prostatic epithelium. This may explain the chromosomal gain on 7q11.2-q31 that is predominantly found in metastasis of prostate tumors. Molecular cytogenetic analysis of prostatic adenocarcinomas indicated an increase in the number of patients showing a gain of chromosome 7pq with increasing tumor volume. These chromosomal alterations are also found in primary tumors that showed progression after radical prostatectomy, suggesting a possible correlation of LIMK1 expression as a biomarker for While the invention has been described, disclosed, illustrated and shown in cancer terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

SEQUENCE LISTING
Sequence of LIM kinase 1                    (SEQ ID NO. 1)
GCGCCGAGCCGGTTTCCCCGCCGGTGTCCGAGAGGCGCCCCCGGCCCG

GCCCGGCCCGGCCCGCGCCCTCCGCCCCCGCC

TCCCCGGGCCGGCGGCGGTGGGCGAGCTCGCGGGCCCGGCCGCCCCC

AGCCCCAGCCCCGCCGGGCCCCGCCCCCCGTCG

AGTGCATGAGGTTGACGCTACTTTGTTGCACCTGGAGGGAAGAACGTA

-continued

```
TGGGAGAGGAAGGAAGCGAGTTGCCCGTGTGT
GCAAGCTGCGGCCAGAGGATCTATGATGGCCAGTACCTCCAGGCCCTG
AACGCGGACTGGCACGCAGACTGCTTCAGGTG
TTGTGACTGCAGTGCCTCCCTGTCGCACCAGTACTATGAGAAGGATGG
GCAGCTCTTCTGCAAGAAGGACTACTGGGCCC
GCTATGGCGAGTCCTGCCATGGGTGCTCTGAGCAAATCACCAAGGGAC
TGGTTATGGTGGCTGGGGAGCTGAAGTACCAC
CCCGAGTGTTTCATCTGCCTCACGTGTGGGACCTTTATCGGTGACGGG
GACACCTACACGCTGGTGGAGCACTCCAAGCT
GTACTGCGGGCACTGCTACTACCAGACTGTGGTGACCCCCGTCATCGA
GCAGATCCTGCCTGACTCCCCTGGCTCCCACC
TGCCCCACACCGTCACCCTGGTGTCCATCCCAGCCTCATCTCATGGCA
AGCGTGGACTTTCAGTCTCCATTGACCCCCCG
CACGGCCCACCGGGCTGTGGCACCGAGCACTCACACACCGTCCGCGTC
CAGGGAGTGGATCCGGGCTGCATGAGCCCAGA
TGTGAAGAATTCCATCCACGTCGGAGACCGGATCTTGGAAATCAATGG
CACGCCCATCCGAAATGTGCCCCTGGACGAGA
TTGACCTGCTGATTCAGGAAACCAGCCGCCTGCTCCAGCTGACCCTCG
AGCATGACCCTCACGATACACTGGGCCACGGG
CTGGGGCCTGAGACCAGCCCCCTGAGCTCTCCGGCTTATACTCCCAGC
GGGGAGGCGGGCAGCTCTGCCCGGCAGAAACC
TGTCTTGAGGAGCTGCAGCATCGACAGGTCTCCGGGCGCTGGCTCACT
GGGCTCCCCGGCCTCCCAGCGCAAGGACCTGG
GTCGCTCTGAGTCCCTCCGCGTAGTCTGCCGGCCACACCGCATCTTCC
GGCCGTCGGACCTCATCCACGGGGAGGTGCTG
GGCAAGGGCTGCTTCGGCCAGGCTATCAAGGTGACACACCGTGAGAC
AGGTGAGGTGATGGTGATGAAGGAGCTGATCCG
GTTCGACGAGGAGACCCAGAGGACGTTCCTCAAGGAGGTGAAGGTCA
TGCGATGCCTGGAACACCCCAACGTGCTCAAGT
TCATCGGGGTGCTCTACAAGGACAAGAGGCTCAACTTCATCACTGAGT
ACATCAAGGGCGGCACGCTCCGGGCATCATC
AAGAGCATGGACAGCCAGTACCCATGGAGCCAGAGAGTGAGCTTTGC
CAAGGACATCGCATCAGGGATGGCCTACCTCCA
CTCCATGAACATCATCCACCGAGACCTCAACTCCCACAACTGCCTGGT
CCGCGAGAACAAGAATGTGGTGGTGGCTGACT
TCGGGCTGGCGCGTCTCATGGTGGACGAGAAGACTCAGCCTGAGGGC
CTGCGGAGCCTCAAGAAGCCAGACCGCAAGAAG
CGCTACACCGTGGTGGGCAACCCCTACTGGATGGCACCTGAGATGATC
AACGGCCGCAGCTATGATGAGAAGGTGGATGT
GTTCTCCTTTGGGATCGTCCTGTGCGAGATCATCGGGCGGGTGAACGC
AGACCCTGACTACCTGCCCCGCACCATGGACT
TTGGCCTCAACGTGCGAGGATTCCTGGACCGCTACTGCCCCCCAAACT
GCCCCCCGAGCTTCTTCCCCATCACCGTGCGC
TGTTGCGATCTGGACCCCGAGAAGAGGCCATCCTTTGTGAAGCTGGAA
CACTGGCTGGAGACCCTCCGCATGCACCTGGC
CGGCCACCTGCCACTGGGCCCACAGCTGGAGCAGCTGGACAGAGGTT
TCTGGGAGACCTACCGGCGCGGCGAGAGCGGAC
TGCCTGCCCACCCTGAGGTCCCCGACTGAGCCAGGGCCACTCAGCTGC
CCCTGTCCCCACCTCTGGAGAATCCACCCCCA
CCAGATTCCTCCGCGGGAGGTGGCCCTCAGCTGGGACAGTGGGGACC
CAGGCTTCTCCTCAGAGCCAGGCCCTGACTTGC
CTTCTCCCACCCCGTGGACCGCTTCCCCTGCCTTCTCTCTGCCGTGGCC
CAGAGCCGGCCCAGCTGCACACACACACCAT
GCTCTCGCCCTGCTGTAACCTCTGTCTTGGCAGGGCTGTCCCCTCTTGC
TTCTCCTTGCATGAGCTGGAGGGCCTGTGTG
AGTTACGCCCCTTTCCACACGCCGCTGCCCCAGCAACCCTGTTCACGC
TCCACCTGTCTGGTCCATAGCTCCCTGGAGGC
TGGGCCAGGAGGCAGCCTCCGAACCATGCCCCATATAACGCTTGGGTG
CGTGGGAGGGCGCACATCAGGGCAGAGGCCAA
GTTCCAGGTGTCTGTGTTCCCAGGAACCAAATGGGGAGTCTGGGGCCC
GTTTTCCCCCCAGGGGGTGTCTAGGTAGCAAC
AGGTATCGAGGACTCTCCAAACCCCCAAAGCAGAGAGAGGGCTGATC
CCATGGGGCGGAGGTCCCCAGTGGCTGAGCAAA
CAGCCCCTTCTCTCGCTTTGGGTCTTTTTTTTGTTTCTTTCTTAAAGCCA
CTTTAGTGAGAAGCAGGTACCAAGCCTCAG
GGTGAAGGGGGTCCCTTGAGGGAGCGTGGAGCTGCGGTGCCCTGGCC
GGCGATGGGGAGGAGCCGGCTCCGGCAGTGAGA
GGATAGGCACAGTGGACCGGGCAGGTGTCCACCAGCAGCTCAGCCCC
TGCAGTCATCTCAGAGCCCCTTCCCGGGCCTCT
CCCCCAAGGCTCCCTGCCCCTCCTCATGCCCCTCTGTCCTCTGCGTTTT
TTCTGTGTAATCTATTTTTTAAGAAGAGTTTT
GTATTATTTTTTCATACGGCTGCAGCAGCAGCTGCCAGGGGCTTGGGA
TTTTATTTTTGTGGCGGGCGGGGGTGGGAGGG
CCATTTTGTCACTTTGCCTCAGTTGAGCATCTAGGAAGTATTAAAACTG
TGAAGCTTTCTCAGTGCACTTTGAACCTGGA
AAACAATCCCAACAGGCCCGTGGGACCATGACTTAGGGAGGTGGGAC
CCACCCACCCCCATCCAGGAACCGTGACGTCCA
AGGAACCAAACCCAGACGCAGAACAATAAAATAAATTCCGTACTCCC
CACCC
```

What is claimed is:

1. A method of treating a subject exhibiting a cancer cell metastasis comprising administering to said subject a therapeutically effective dose of a composition comprising an antisense ribonucleic acid (RNA) that targets SEQ ID NO. 1.

2. The method of claim 1, wherein said cancer cell metastasis comprises prostate cancer cells.

3. The method of claim 1, wherein said cancer cell metastasis comprises ovarian cancer cells.

4. The method of claim 1, wherein said cancer cell metastasis comprises breast cancer cells.

5. The method of claim 1, wherein said cancer cell metastasis comprises lung cancer cells.

6. The method of claim 1, wherein said administering is transdermal, intravenous, intraperitoneal or implanted adminstration.

7. The method of claim 1 wherein said subject is experiencing a recurrence of prostate cancer, and said administering comprises reducing the proliferation of prostate cancer cells.

* * * * *

SEQUENCE LISTING

<160> NUMBER OF SEQ ID NOS: 3

<210> SEQ ID NO 1
<211> LENGTH: 3332
<212> TYPE: DNA
<213> ORGANISM: Homo sapiens

<400> SEQUENCE: 1

```
gcgccgagcc ggtttccccg ccggtgtccg agaggcgccc ccggcccggc ccggcccggc      60
ccgcgccctc cgccccccgcc tccccgggcc ggcggcggtg ggcgagctcg cgggcccggc     120
cgcccccagc cccagccccg ccgggccccg cccccgtcg agtgcatgag gttgacgcta      180
ctttgttgca cctggaggga agaacgtatg ggagaggaag gaagcgagtt gcccgtgtgt     240
gcaagctgcg gccagaggat ctatgatggc cagtacctcc aggccctgaa cgcggactgg     300
cacgcagact gcttcaggtg ttgtgactgc agtgcctccc tgtcgcacca gtactatgag     360
aaggatgggc agctcttctg caagaaggac tactgggccc gctatggcga gtcctgccat     420
gggtgctctg agcaaatcac caagggactg gttatggtgg ctggggagct gaagtaccac     480
cccgagtgtt tcatctgcct cacgtgtggg acctttatcg gtgacgggga cacctacacg     540
ctggtggagc actccaagct gtactgcggg cactgctact accagactgt ggtgaccccc     600
gtcatcgagc agatcctgcc tgactcccct ggctcccacc tgccccacac cgtcaccctg     660
gtgtccatcc cagcctcatc tcatggcaag cgtggacttt cagtctccat tgaccccccg     720
cacggcccac cgggctgtgg caccgagcac tcacacaccg tccgcgtcca gggagtggat     780
ccgggctgca tgagcccaga tgtgaagaat tccatccacg tcggagaccg gatcttggaa     840
atcaatggca cgcccatccg aaatgtgccc ctggacgaga ttgacctgct gattcaggaa     900
accagccgcc tgctccagct gaccctcgag catgaccctc acgatacact gggccacggg     960
ctggggcctg agaccagccc cctgagctct ccggcttata ctcccagcgg ggaggcgggc    1020
agctctgccc ggcagaaacc tgtcttgagg agctgcagca tcgacaggtc tccgggcgct    1080
ggctcactgg gctccccggc ctcccagcgc aaggacctgg gtcgctctga gtccctccgc    1140
gtagtctgcc ggccacaccg catcttccgg ccgtcggacc tcatccacgg ggaggtgctg    1200
ggcaagggct gcttcggcca ggctatcaag gtgacacacc gtgagacagg tgaggtgatg    1260
gtgatgaagg agctgatccg gttcgacgag gagacccaga ggacgttcct caaggaggtg    1320
aaggtcatgc gatgcctgga acaccccaac gtgctcaagt tcatcggggt gctctacaag    1380
gacaagaggc tcaacttcat cactgagtac atcaagggcg gcacgctccg gggcatcatc    1440
aagagcatgg acagccagta cccatggagc cagagagtga gctttgccaa ggacatcgca    1500
tcagggatgg cctacctcca ctccatgaac atcatccacc gagacctcaa ctcccacaac    1560
tgcctggtcc gcgagaacaa gaatgtggtg tggctgactg tcgggctggc gcgtctcatg    1620
gtggacgaga agactcagcc tgagggcctg cggagcctca agaagccaga ccgcaagaag    1680
cgctacaccg tggtgggcaa ccctactgg atggcacctg agatgatcaa cggccgcagc    1740
tatgatgaga aggtggatgt gttctccttt gggatcgtcc tgtgcgagat catcgggcgg    1800
gtgaacgcag accctgacta cctgcccgc accatggact ttggcctcaa cgtgcgagga    1860
ttcctggacc gctactgccc cccaaactgc ccccgagct tcttccccat caccgtgcgc    1920
tgttgcgatc tggaccccga gaagaggcca tcctttgtga agctgaaca ctggctggag    1980
accctccgca tgcacctggc cggccacctg ccactgggcc cacagctgga gcagctggac    2040
```

```
agaggtttct gggagaccta ccggcgcggc gagagcggac tgcctgccca ccctgaggtc    2100
cccgactgag ccagggccac tcagctgccc ctgtccccac ctctggagaa tccaccccca    2160
ccagattcct ccgcgggagg tggccctcag ctgggacagt ggggacccag gcttctcctc    2220
agagccaggc cctgacttgc cttctcccac cccgtggacc gcttcccctg ccttctctct    2280
gccgtggccc agagccggcc cagctgcaca cacacaccat gctctcgccc tgctgtaacc    2340
tctgtcttgg cagggctgtc ccctcttgct tctccttgca tgagctggag ggcctgtgtg    2400
agttacgccc ctttccacac gccgctgccc cagcaaccct gttcacgctc cacctgtctg    2460
gtccatagct ccctggaggc tgggccagga ggcagcctcc gaaccatgcc ccatataacg    2520
cttgggtgcg tgggagggcg cacatcaggg cagaggccaa gttccaggtg tctgtgttcc    2580
caggaaccaa atggggagtc tggggcccgt tttccccccca gggggtgtct aggtagcaac    2640
aggtatcgag gactctccaa accccaaag cagagagagg gctgatccca tggggcggag    2700
gtccccagtg gctgagcaaa cagcccttc tctcgctttg ggtcttttt ttgtttcttt    2760 cttaaagcca ctttagtgag aagcaggtac caagcctcag ggtgaagggg gtcccttgag    2820
ggagcgtgga gctgcggtgc cctggccggc gatggggagg agccggctcc ggcagtgaga    2880
ggataggcac agtggaccgg gcaggtgtcc accagcagct cagcccctgc agtcatctca    2940
gagccccttc ccgggcctct cccccaaggc tccctgcccc tcctcatgcc cctctgtcct    3000
ctgcgttttt tctgtgtaat ctattttta agaagagttt gtattatttt ttcatacggc    3060
tgcagcagca gctgccaggg gcttgggatt ttatttttgt ggcgggcggg ggtgggaggg    3120
ccattttgtc actttgcctc agttgagcat ctaggaagta ttaaaactgt gaagctttct    3180
cagtgcactt tgaacctgga aaacaatccc aacaggcccg tgggaccatg acttagggag    3240
gtgggaccca cccaccccca tccaggaacc gtgacgtcca aggaaccaaa cccagacgca    3300
gaacaataaa ataaattccg tactccccac cc                                 3332
```

```
<210> SEQ ID NO 2
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gacgacgaca agatggcctc cggtgtggct g                                  31

<210> SEQ ID NO 3
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gaggagaagc ccggttcaca aaggcttgcc c                                  31
```